US011951327B2

(12) United States Patent
Garonna et al.

(10) Patent No.: US 11,951,327 B2
(45) Date of Patent: Apr. 9, 2024

(54) HEART ARRHYTHMIA NON-INVASIVE TREATMENT DEVICE AND METHOD

(71) Applicant: EBAMed SA, Geneva (CH)

(72) Inventors: Adriano Garonna, Geneva (CH); Giovanni Leo, Cologny (CH)

(73) Assignee: EBAMed SA, Geneva (CH)

( * ) Notice: Subject to any disclaimer, the term of this patent is extended or adjusted under 35 U.S.C. 154(b) by 0 days.

(21) Appl. No.: 17/717,310

(22) Filed: Apr. 11, 2022

(65) Prior Publication Data

US 2022/0305288 A1 Sep. 29, 2022

Related U.S. Application Data

(63) Continuation of application No. 16/764,967, filed as application No. PCT/EP2018/081455 on Nov. 15, 2018, now Pat. No. 11,298,565.

(30) Foreign Application Priority Data

Nov. 16, 2017 (EP) ..................................... 17202164

(51) Int. Cl.
*A61N 5/00* (2006.01)
*A61N 5/10* (2006.01)
*G16H 40/60* (2018.01)

(52) U.S. Cl.
CPC ......... *A61N 5/1037* (2013.01); *A61N 5/1049* (2013.01); *A61N 5/1068* (2013.01);
(Continued)

(58) Field of Classification Search
None
See application file for complete search history.

(56) References Cited

U.S. PATENT DOCUMENTS

| 5,590,657 A | 1/1997 | Cain et al. |
| 5,718,241 A | 2/1998 | Ben-Haim et al. |

(Continued)

FOREIGN PATENT DOCUMENTS

| CA | 2781536 A1 | 12/2012 |
| JP | 2016214438 A | 12/2016 |

(Continued)

OTHER PUBLICATIONS

Prall et al. "Treatment of arrhythmias by external charged particle beams: a Langendorff feasibility study" Biomed. Eng.—Biomed. Tech. 60(2) pp. 147-156 (2015).

(Continued)

*Primary Examiner* — Hoon K Song
(74) *Attorney, Agent, or Firm* — Eversheds Sutherland (US) LLP; Christopher C. Bolten; Nicola A. Pisano

(57) ABSTRACT

The present invention relates to a heart tissue ablation device comprising a charged particle emitting system 1, a control system 2 for instructing the accelerator and beamline when to create the beam and what its required properties should be, a patient positioning and verification system, an ultrasound cardiac imaging system 3 performed on the patient, able to track the target movement, a computer program to determine and record the safe motion margins, the treatment plans for one or more motion phases and a computer program to regulate the control system 2 to load the correct irradiation plan according to the motion phase and if the position of the target is inside of the position margin, the irradiation is enabled and if the position of the target is outside of the position margin, the irradiation is disabled.

20 Claims, 1 Drawing Sheet

(52) U.S. Cl.
CPC ..... *G16H 40/60* (2018.01); *A61N 2005/1058* (2013.01); *A61N 2005/1061* (2013.01); *A61N 2005/1087* (2013.01); *A61N 2005/1097* (2013.01)

(56) References Cited

U.S. PATENT DOCUMENTS

| | | | |
|---|---|---|---|
| 5,764,723 | A | 6/1998 | Weinberger et al. |
| 6,144,875 | A | 11/2000 | Schweikard et al. |
| 6,658,285 | B2 | 12/2003 | Potse et al. |
| 6,710,362 | B2 | 3/2004 | Kraft et al. |
| 6,780,152 | B2 | 8/2004 | Üstüner et al. |
| 6,863,653 | B1 | 3/2005 | Zanelli et al. |
| 6,889,695 | B2 | 5/2005 | Pankratov et al. |
| 7,260,426 | B2 | 8/2007 | Schweikard et al. |
| 7,346,381 | B2 | 3/2008 | Okerlund et al. |
| 7,853,313 | B2 | 12/2010 | Thomson |
| 7,953,204 | B2 | 5/2011 | Sumanaweera et al. |
| 8,295,906 | B2 | 10/2012 | Saunders et al. |
| 8,351,571 | B2 | 1/2013 | Brinks et al. |
| 8,792,613 | B2 | 7/2014 | Gardner et al. |
| 8,805,481 | B2 | 8/2014 | Sumanaweera et al. |
| 9,014,424 | B2 | 4/2015 | Berlinger et al. |
| 9,108,048 | B2 | 8/2015 | Maurer, Jr. et al. |
| 9,289,268 | B2 | 3/2016 | Ramraj et al. |
| 9,320,916 | B2 | 4/2016 | Sumanaweera et al. |
| 9,326,751 | B2 | 5/2016 | Hastings |
| 9,504,853 | B2 | 11/2016 | Sumanaweera et al. |
| 9,789,339 | B2 | 10/2017 | Moskvin et al. |
| 9,907,978 | B2 | 3/2018 | Pankratov et al. |
| 9,968,801 | B2 | 5/2018 | Sumanaweera et al. |
| 10,265,543 | B2 | 4/2019 | Bharat et al. |
| 10,286,228 | B2 | 5/2019 | Bharat et al. |
| 10,342,558 | B2 | 7/2019 | Steckner et al. |
| 10,363,439 | B2 | 7/2019 | Amaldi |
| 10,485,992 | B2 | 11/2019 | Heese et al. |
| 10,548,496 | B2 | 2/2020 | Gijsbers et al. |
| 2002/0095197 | A1 | 7/2002 | Lardo et al. |
| 2004/0015075 | A1 | 1/2004 | Kimchy et al. |
| 2004/0162596 | A1 | 8/2004 | Altshuler et al. |
| 2005/0171396 | A1 | 8/2005 | Pankratov et al. |
| 2006/0241443 | A1 | 2/2006 | Horvath et al. |
| 2006/0224053 | A1 | 10/2006 | Black et al. |
| 2008/0021300 | A1 | 1/2008 | Allison |
| 2008/0023644 | A1 | 1/2008 | Pedroni |
| 2008/0177279 | A1* | 7/2008 | Sumanaweera ........ A61B 90/36 901/41 |
| 2009/0076373 | A1 | 3/2009 | Maschke |
| 2009/0180589 | A1* | 7/2009 | Wang .................. A61N 5/1082 378/65 |
| 2009/0234237 | A1 | 9/2009 | Ross et al. |
| 2009/0238404 | A1 | 9/2009 | Orderud et al. |
| 2009/0253102 | A1 | 10/2009 | Porikli et al. |
| 2010/0016765 | A1 | 1/2010 | Hall et al. |
| 2010/0145358 | A1 | 6/2010 | Maschke |
| 2010/0217139 | A1 | 8/2010 | Pinter et al. |
| 2010/0239066 | A1 | 9/2010 | Fahrig et al. |
| 2010/0282983 | A1 | 11/2010 | Wright et al. |
| 2010/0317968 | A1 | 12/2010 | Wright et al. |
| 2011/0107270 | A1 | 5/2011 | Wang et al. |
| 2011/0160566 | A1 | 6/2011 | Petropoulos et al. |
| 2011/0185503 | A1* | 8/2011 | Yan ...................... A61N 5/1049 5/601 |
| 2012/0004518 | A1 | 1/2012 | D'Souza et al. |
| 2012/0134233 | A1 | 5/2012 | Lin et al. |
| 2012/0146641 | A1 | 6/2012 | Wu et al. |
| 2012/0181428 | A1 | 7/2012 | Bert et al. |
| 2012/0316423 | A1 | 12/2012 | Raleigh et al. |
| 2012/0323233 | A1 | 12/2012 | Maguire et al. |
| 2013/0035682 | A1 | 2/2013 | Weil |
| 2013/0079645 | A1 | 3/2013 | Amirana et al. |
| 2013/0211482 | A1 | 8/2013 | Piipponen |
| 2013/0237822 | A1 | 9/2013 | Gross et al. |
| 2014/0005463 | A1 | 1/2014 | Jongen |
| 2014/0107390 | A1 | 4/2014 | Brown et al. |
| 2014/0316247 | A1 | 10/2014 | Hwang et al. |
| 2015/0080634 | A1 | 3/2015 | Huber et al. |
| 2015/0112197 | A1* | 4/2015 | Bharat ................ A61N 5/1037 600/3 |
| 2015/0150643 | A1 | 6/2015 | Trayanova et al. |
| 2015/0182760 | A1 | 7/2015 | Raleigh et al. |
| 2015/0290472 | A1 | 10/2015 | Maguire et al. |
| 2015/0343238 | A1* | 12/2015 | Balakin ............... A61N 5/1082 600/1 |
| 2016/0000409 | A1 | 1/2016 | Bruder et al. |
| 2016/0058368 | A1 | 3/2016 | Swaminathan et al. |
| 2016/0082284 | A1 | 3/2016 | Ooga et al. |
| 2016/0114189 | A1 | 4/2016 | Mihailescu |
| 2016/0121142 | A1 | 5/2016 | Zhang et al. |
| 2016/0184610 | A1 | 6/2016 | Porikli |
| 2016/0331262 | A1 | 11/2016 | Kuck et al. |
| 2016/0338676 | A1 | 11/2016 | Berger et al. |
| 2017/0014642 | A1 | 1/2017 | An et al. |
| 2017/0014645 | A1 | 1/2017 | Foo et al. |
| 2017/0042515 | A1 | 2/2017 | Schwartz et al. |
| 2017/0080253 | A1 | 3/2017 | Clayton |
| 2017/0106208 | A1 | 4/2017 | Gauthier et al. |
| 2017/0128744 | A1 | 5/2017 | Adler et al. |
| 2018/0153467 | A1 | 6/2018 | Lichtenstein et al. |
| 2018/0214713 | A1 | 8/2018 | Dehghan Marvast et al. |
| 2018/0318606 | A1 | 11/2018 | Robinson et al. |
| 2020/0090345 | A1 | 3/2020 | Krebs et al. |
| 2020/0179722 | A1* | 6/2020 | Packer .................... G06T 7/149 |

FOREIGN PATENT DOCUMENTS

| | | |
|---|---|---|
| WO | WO0126569 A1 | 4/2001 |
| WO | WO2013179221 | 12/2013 |
| WO | WO2015053737 A1 | 4/2015 |
| WO | WO2017066358 A1 | 4/2017 |
| WO | WO2017078757 | 5/2017 |

OTHER PUBLICATIONS

Lehmann et al. "Feasbility Study on Cardia Arrhythmia Ablation Using High-Energy Heavy Ion Beams" Nature/ Scientific Reports 6:38895 | DOI: 10.1038/srep38895 (2016) 13 pages.

Graeff, et al. "a 4D-optimization concept for scanned ion beam therapy" Radiotherapy and Oncology 109 (2013) pp. 419-424.

Lis, et al. "A modular dose delivery system for treating moving targets with scanned ion beams: Performance and safety characteristics, and preliminary tests" Physica Medica 76 (2020) pp. 307-316.

Fiorito, et al. "Detection of Cardiac Events in Echocardiography in 3D Convolutional Recurrent Neural Networks" (2018) 4 pages.

Bai, et al. "An Empirical Evaluation of Generic Convolutional and Recurrent Networks for Sequence Modeling" (2018) 14 pages.

Kingma, et al. "Adam: A Method for Stochastic Optimization" *Published as a conference paper at ICLR* (2015) 15 pages.

Devries, et al. "Improved Regularization of Convolutional Neural Networks with Cutout" *University of Guelph Canadian Institute for Advanced Research and Vector Institute* (2017) 8 pages.

Zei, et al. "Ablative Radiotherapy as a Noninvasive Alternative to Catheter Ablation for Cardiac Arrhythmias" *Curr Cardiol Rep* (2017) 9 pages.

CN Office Action in Application No. 201880085503.X dated Dec. 13, 2021 (10 pages.).

* cited by examiner

HEART ARRHYTHMIA NON-INVASIVE TREATMENT DEVICE AND METHOD

RELATED APPLICATIONS

This application is a continuation of U.S. patent application Ser. No. 16/764,967, filed May 18, 2020, which is a national stage entry of PCT/EP2018/081455, filed Nov. 15, 2018, which claims the benefit of EP17202164.4, filed Nov. 16, 2017. The disclosures of which are incorporated by reference herein in their entireties.

TECHNICAL FIELD OF THE INVENTION

The present invention relates to a method and a device for treating arrhythmias. More particularly, the present invention relates to a method and a device for treating arrhythmias in a non-invasive way.

BACKGROUND

Heart arrhythmias are disruptions in the normal heartbeat. They affect more than 2% of the general population in Europe and are expected to at least double in the next 50 years as the population ages. Their occurrence is strongly linked to risks of heart attacks and strokes.

More particularly, heart arrhythmia is a problem with the rate or rhythm of the heartbeat. It means that the heart beats too quickly, too slowly, or with an irregular pattern. The heart beating faster than normal, above 100 beats per minute in adults, is called tachycardia. The heart beating too slowly, below 60 beats per minute, is called bradycardia. The most common type of arrhythmia is atrial fibrillation, which causes an irregular and fast heartbeat. Many factors can affect your heart's rhythm, such as having had a heart attack, smoking, congenital heart defects, and stress. Some substances or medicines may also cause arrhythmias.

Treatments may include medications, medical procedures such as ablation or implantation of a pacemaker or defibrillator, and surgery. Medications for a fast heart rate may include beta-blockers or agents that attempt to restore a normal heart rhythm such as procainamide. This latter group may have more significant side effects especially if taken for a long period of time. Pacemakers are often used for slow heart rates. Those with an irregular heartbeat are often treated with blood thinners to reduce the risk of complications. Those who have severe symptoms from an arrhythmia may receive urgent treatment with a controlled electric shock in the form of cardioversion or defibrillation.

Further, ablations are often used to treat arrhythmias. They consist in burning specific heart tissues with invasive tools such as catheters, to stop the conduction of the disrupted electrical signals. These invasive catheter ablation procedures are surgical interventions performed manually and the treatment efficacy varies largely from 50% to 80% according to the technology used and skill of the medical doctor. Moreover, the procedures require many hours and are at risk of serious complications like tissue perforation, vein stenosis or creation of a blood clot. The low quality of the lesion created by catheter ablation results in procedures which have to be repeated successive times, with increasing complexity for the medical staff and risk for the patient.

There is therefore a need for a method of treatment of cardiac arrhythmias via non-invasive ablation.

Charged particle beams are presently used for the treatment of tumors and occur in 20-30 sessions in successive days. These charged particle beams have the physical characteristic of depositing most of their energy in the last few millimeters of their path (so-called Bragg peak). By adjusting the beam's transverse position and energy, any target 3D volume can be precisely covered, sparing surrounding healthy tissues.

It has therefore been investigated how to provide a heart tissue ablating device and method comprising emitting beams of charged particles (mainly protons but also carbon, oxygen and helium ions) for ablating the said heart tissue.

However, since the position of the Bragg peak depends on the density of the body tissues traversed, any motion due to the patient's physiological inner movements such as respiration, heartbeat, digestion or else can result in a difference of density encountered by the incoming proton beam and therefore a different position of the Bragg peak. The precision of irradiation with charged particle beams is therefore strongly sensitive to motion of the target. This is one of the reasons why current charged particle beam treatments are mostly limited to the head, the neck, the hip region and more rarely, the trunk (pancreas, liver and lung).

There is therefore a need for a non-invasive device and a non-invasive method of treatment of cardiac arrhythmias via ablation based on charged particle beams, which can be adjusted to the body motion in real time to provide a safe and effective treatment.

SUMMARY OF THE INVENTION

The above problems are solved by the present invention.

According to a first aspect of the present invention, the treatment system is therefore composed of an accelerator and beam line, which create the required beam with given properties (intensity, position, angle and/or energy), of a control system to instruct the accelerator and beamline when to create the beam and what its required properties should be, of a patient positioning system, which comprises a robotic apparatus upon which the patient is immobilized, to position the patient and of an imaging system (based on double X-rays or Cone-beam Computer Tomography (CT)) to verify the patient positioning.

Animal trials have shown that charged particle beams can be used to ablate heart tissue. However, in order to ensure a safe, effective and fast procedure, the system of the present invention is able to monitor in real-time the motion of the patient inner tissues, to infer the motion of the treatment target and to adapt in consequence the beam delivery based on a pre-established motion model. The motion model informs about the allowed target position for some defined motion phases (one or more), which correspond to a combination of phases of the respiratory and cardiac cycles. This can involve 'gating' the beam when the position detected by the imaging system of the target is not as expected from the motion model for that given motion phase and cannot be compensated by the irradiation system, and 'tracking', i.e. adapting the beam transverse and longitudinal characteristics based on the identified motion phase.

Advantageously, the system is composed of a hardware and a software part. The imaging is performed fully non-invasively, i.e. it does not require to implant fiducial markers or to insert the imaging system inside the body cavities, and shall not be placed in the path of the charged particle beams.

In this regard, one or more ultrasound imaging systems are placed externally on the patient body in order to image the heart region from the abdominal or thoracic viewing windows. Imaging can be performed using one or more linear arrays, phased arrays, multi-plane arrays (also called T-shaped or X-plane) and matrix arrays ultrasound transducers to acquire 2D or 3D images at frame rates higher than the heartbeat.

These devices are used to simultaneously image parts of the heart. By knowing the position of each imaging system inside the treatment room (using for example optical markers on each imaging device and optical cameras, or magnetic sensors), one can relate the position of an object in the image to its position in 3D space. Possibly coupled with respiratory and cardiac motion sensors, this allows to detect the phase of the motion of the target and its displacement from the nominal position, which is defined in the planning.

Planning relies on performing 4D-CT (time-resolved computed tomography) scans (possibly with respiratory and cardiac sensors) to determine for one or more phases of respiratory and cardiac cycles the target for the ablation and the required beam properties (angle, energy, position, intensity) to effectively irradiate the target while sparing sensitive surrounding healthy tissues. The CTs are taken for different phases of the respiratory and cardiac cycles, in order to determine the motion of the target during respiratory and cardiac cycles. Based on this information, boundaries around the clinical target volume(s) are defined and together constitute the 'nominal' target positions. Simultaneously or at a separate time, the ultrasound imaging system (and possibly an MR system) records images of either the target regions themselves or near-by tissues for all cardiac and respiratory phases. These are used to determine a motion model: the model consists in a set of points (so-called fiducials) in ultrasound images and for each fiducial, their nominal position in space. The fiducial positions depend on the respiratory and cardiac phase and can be directly univocally correlated to the position of the ablation target. For easy visualization, the ultrasound images (and possibly MR images) can be fused to the 4D-CT images for easy identification of the structures for the medical operator.

The device and the system of the invention are convenient for the patient since they consist in a non-invasive procedure lasting less than two hours without anesthesia in a single or at worst few out-patient sessions. The invention is effective since the deep ablation of both inner and outer cardiac muscle tissue consists in continuous 3D volumes instead of the ablation points/lines performed by today's technology. Finally, they provide a risk reduction because there is no risk of infection due to surgery and do not result in the deposition of large doses to healthy tissues, contrary to ablation with X-ray/Gamma-ray/Photon beams (typically used in so-called conventional radiotherapy for the treatment of tumors).

BRIEF DESCRIPTION OF THE DRAWINGS

Further particular advantages and features of the invention will become more apparent from the following non-limitative description of at least one embodiment of the invention which will refer to the accompanying drawings, wherein.

DETAILED DESCRIPTION OF THE INVENTION

Figure 1:
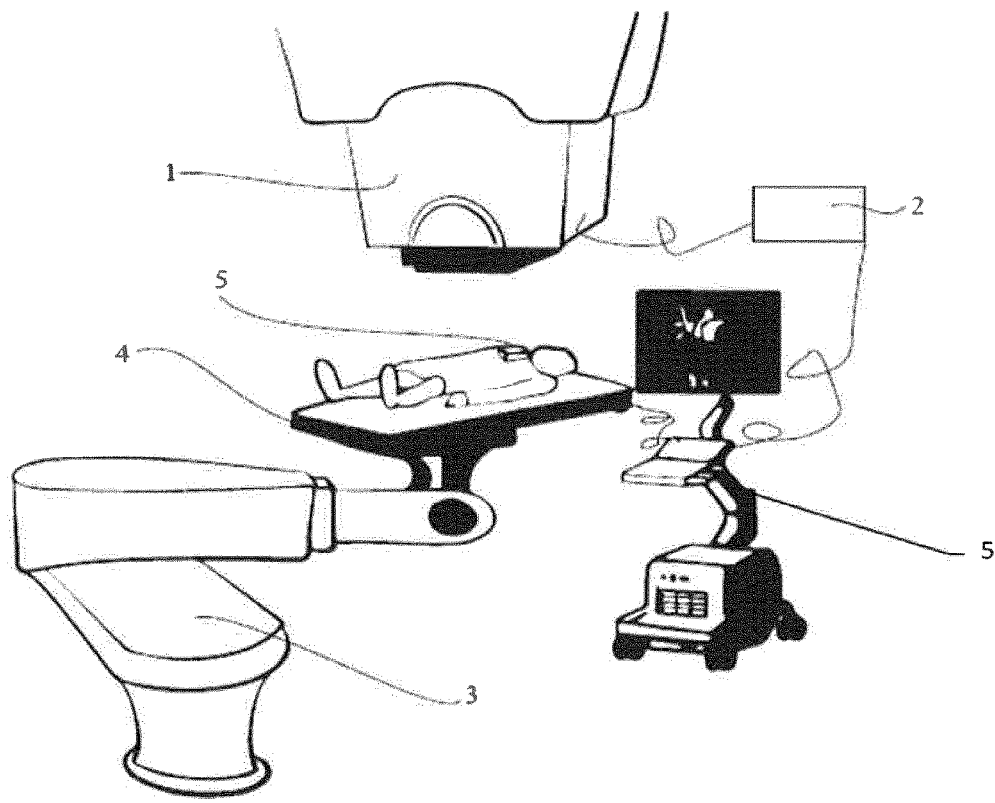
FIG. 1 represents a heart arrhythmia treatment device according to a preferred embodiment of the present invention.
Figure 2:
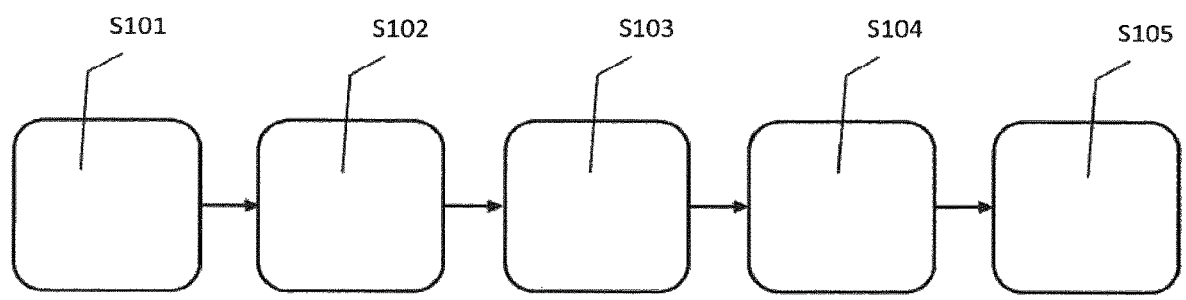
FIG. 2 schematically represents heart arrhythmia treatment method according to a preferred embodiment of the present invention.

The present detailed description is intended to illustrate the invention in a non-limitative manner since any feature of an embodiment may be combined with any other feature of a different embodiment in an advantageous manner.

In the following description several terms are used in a specific way which are defined below:

The expression 'treatment/irradiation plan' refers to the patient-specific list of treatment properties (treatment room, type and position of the patient positioning system, beam species, irradiation angle, beam size, beam position, beam energy, beam intensity, number of treatment sessions, among others) in order to irradiate the appropriate volume in the patient body with the required therapeutic radiation dose. These properties are computed based on the planning CT (static or time-resolved), where the medical staff has defined the clinical target which should receive a given dose, the critical healthy tissues that should be irradiated in the least possible fashion and the margins around the clinical target that consider the possible errors related to patient positioning and motion during the delivery.

The term 'gating' refers to sending a binary signal (optical, electrical, among others) to the beam delivery system to either: pause the irradiation or resume the irradiation as planned.

The term 'tracking' refers to sending a signal to the beam delivery system to modify the irradiation beam properties (transverse size, longitudinal size, transverse position, energy, intensity, among others) in order to match the recorded motion of the irradiation target.

The term 'reference structures' refers to segmented elements (point, open line, closed line, volume) from the ultrasound images taken at planning stage, whose position in all motion phases is computed and compared (for each motion phase) to the position of the irradiation target structure in the planning CT images.

The term 'fiducials' refers to a sub-set of the 'reference structures' characterized by the fact that their motion can be univocally correlated to the motion of the irradiation target in the planning CT images, as is the case if the difference in position between the fiducial in the ultrasound image and the irradiation target in the planning CT image is constant for all motion phases.

The expression 'nominal positions' refers to the position of the fiducial(s) established in the planning phase. This is univocally also correlated to the position of the target in the planning CT.

The expression 'motion boundaries' refers to margins taken around the clinical target volume to account for allowed motion. These depend on the critical surrounding healthy tissues and on how the motion is modelled and mitigated. For example, a possible approach is to consider only one phase of the respiratory and cardiac cycles and take large margins for the allowed motion, in order to have a large gating window. Another approach is to consider many phases of the respiratory and cardiac cycles and take small margins for the allowed motion, in order to track the motion and limit the irradiation of healthy tissues surrounding the clinical target.

The expression 'respiratory and cardiac sensors' refers to any (optical, electrical, magnetic, acoustic, among others) means to infer the present respiratory cycle phase and cardiac cycle phase. This includes also a simple time counter, which in a predictive manner can determine which is the current phase of the respiratory and cardiac cycles based on established regular patterns for the specific patient.

The ablating device of the present invention is composed of a charged particle emitting system 1, which preferably comprises an accelerator, and a beamline, which create the required beam with a given intensity, position, angle and energy.

It further comprises a control system 2 for instructing the accelerator and beamline when to create the beam and what its required properties should be.

It also comprises a patient positioning system 3, which comprises a robotic apparatus 4 to position the patient and an imaging system (based on double X-rays or Cone-beam CT) to verify the patient positioning.

In addition to this, to be able to track the target motion, the ablating device further comprises an ultrasound cardiac imaging system 5 including a probe, connected to a movable tray with hardware control and signal processing units and a CPU, preferably with a screen (possibly combined with ECG (electrocardiogram) and respiration monitoring).

The control system 2 is then regulated by the results of the ultrasound imaging systems 5 during the treatment.

Of course, other additional modalities are also possible: MRI, ECGI, among others.

Ablation Process

The ablation process is as follows.

First, a treatment plan is defined. That is, the 3D target volume (~2-200 cm$^3$), the target motion, the therapeutic dose (~20-60 Gy), the irradiation angle(s) and critical tissues and their dose limits have to be calculated and defined. The treatment plan is performed for one or more respiratory and cardiac cycle phases. For each of these, the treatment plan includes an irradiation plan for the clinical target position and its allowed motion boundaries, within which the treatment can be considered safe.

More particularly, this planning step S101 comprises first taking ultrasound and CT images of the heart either simultaneously or one after the other for all cardiac and respiratory cycles, contouring by a medical staff of the target region in CT images for one or more motion phases (a motion phase can combine various respiratory and cardiac cycle phases), determining the beam irradiation parameters for each of the chosen motion phases based on the target region and surrounding healthy tissues, determining, for each of the chosen motion phases, boundaries for the target region outside of which irradiation should be stopped because it is unsafe. Successively, planning consists in performing an image segmentation on ultrasound images, co-registering/fusing the ultrasound images with MRI or CT images where the target region appears, selecting one or more fiducials (from all the automatically segmented reference points/lines in the ultrasound frames based on their stability of relative position with respect to the target regions for all defined motion phases), and recognizing the corresponding positions of the fiducials in all the other data frames of the ultrasound images.

On the treatment day, a patient positioning step S102 is carried out where a patient is positioned in the treatment room via immobilization devices on a treatment table/chair. The table/chair is robotized in order to hold a specific position and to, on command, perform translations and/or rotations in space.

Then, once the patient is positioned, a patient position verification step S103 is carried out where the patient position is verified through embarked in-room Computer Tomography (CT) or double X-ray imaging. If the position is different from the expected one, the patient position is modified using the robotized table/chair. A re-verification of the patient position may be performed.

The previous steps are repeated iteratively until it is verified that the patient position is the same as when the CT imaging (of the previous planning step) took place. Once the patient position is verified and judged correct, the irradiation S104 starts: a single irradiation is emitted at prescribed angle of prescribed volume of the heart (as determined during treatment planning) together with non-invasive imaging via an ultrasound system consisting of one or multiple ultrasound transducers placed out of the irradiation field, possibly combined with cardiac and respiratory cycle sensors.

Then a judgment step S105 is carried out, where based on the imaging, the target position is determined in real-time, the relevant motion phase is identified and the target position is compared to its nominal position and its motion boundaries.

More particularly, based on the imaging, and possibly aided by cardiac (ECG) and respiratory (monitoring of abdomen movement for example) cycle monitoring, the system recognizes the relevant motion phase of the 4D-CT and thus the relevant irradiation plan for that phase. It should be understood of course that in the case that the treatment plan is done for only one motion phase, the loading of the irradiation plan does not correspond to any change in the control system 2 since there is, in such case, no irradiation plan choice as single one is available. This is achieved through image segmentation and registration on ultrasound images to determine the position of the fiducials (reference points/lines) on the ultrasound images and thus to derive from them the relevant irradiation plan. The system then sends this information to the control system 2 to set up the machine for irradiation with the correct beam parameters. The system also compares the determined fiducial positions to the nominal positions for safe irradiation for that particular irradiation plan and finally, in case the difference in position is smaller than the pre-established margin, it sends a gating signal to the control system 2 to allow irradiation or in case the difference in position is larger than the pre-established margin, sends a gating signal to the control system 2 to pause the irradiation.

In other words, based on the imaging, the beam target position is determined in real-time and compared to an expected position according to a motion model defined in the treatment planning. If the beam target position is outside of pre-established boundaries, the beam irradiation is gated (paused). If the position is within the boundaries (for example within a sphere of 1 mm radius from the nominal position of a particular fiducial point), irradiation is allowed and the beam characteristics correspond to those of a pre-established treatment plan. A safety system is integrated which stops irradiation if movement is outside of given boundaries (for example, when the motion of the earlier given fiducial point is larger than 1 mm from the nominal position).

As explained above, the irradiation system comprises an accelerator and a beamline to provide the beam of accelerated charged particles of the correct properties (size, intensity, energy, position). The beamline can be mounted on a rotating mechanical frame (gantry) to change the angle of irradiation. All beam properties are controlled by the control system 2 based on the off-line planned treatment and motion model and on the on-line monitoring of both the beam position and intensity and the target motion.

In the case of irradiation with multiple angles, when irradiation is completed for one gantry angle, irradiation is stopped and the gantry is rotated to the new pre-determined angle. If needed, the patient positioning and position verification step are performed. Then, the irradiation step is performed for this new angle.

The imaging system and process will now be explained more in details.

Ultrasound Tracking System and Method

The ultrasound system of the present invention is preferably composed of one or multiple 2D or 3D ultrasound transducers for continuous visualization of the heart transabdominally/thoracically, i.e. between ribs and/or through liver for all time frames (10-30 Hz). Positioning and tuning of the devices can be made by an operator but a holding system shall enable to fix the position for long continuous acquisition times, e.g. about 1 to 2 hours, with only remote supervision and/or control.

The transducer(s) and/or its support system have optical or magnetic markers so as to be able to geolocalize and continuously monitor their position in the treatment/imaging room coordinate frame and to fuse/co-register their image to CT and MR images. Thus, the transducer position in space can be measured and tracked in order to associate the registered fiducials with the corresponding structure in the CT or MR image. The ultrasound imaging system is such that it can withstand operation with radiation exposure (indirect emission of neutrons and gamma rays from the incoming treatment beam). Alternatively, in case the data processing cannot be put in the treatment/imaging room, the signal can be transported with negligible loss towards a nearby area via analogic or digital data transmission cables.

The ultrasound system can be co-adjuvated by monitoring systems for the cardiac (ECG) and respiratory cycles (optical abdomen motion monitoring for example).

In the case of atrial fibrillation, the target region for ablation is typically around the pulmonary veins at their intersection with the left atrium. The ultrasound-based tracking system could thus aim at visualizing the left atrium and the pulmonary veins. The atrium wall could be used to quantify the motion of the pulmonary veins and/or Doppler ultrasound imaging could be used to image the blood flow and thus indirectly determine the position of the veins. In the case of ventricular tachycardia, the target region for ablation could be determined by late gadolinium enhanced MRI and/or electrophysiological mapping using mapping catheters and/or electrocardiographic imaging (ECGI). The ultrasound-based tracking system would thus aim at visualizing for example the ventricular outer wall and/or the ventricular septum.

A first, offline, computer program runs before the ablation treatment and enables to automatically segment the ultrasound images, discard some structures based on user-given criteria keeping only 'reference' structures and co-register/fuse the reference structures to the CT images for one of the respiratory and cardiac motion phases used for the treatment planning. The computer program then performs an image segmentation and registration for all the other motion phases to establish the new position of the reference structures and co-registers/fuses the position of the structures to the CT images for the same motion phase. The computer then determines the structure(s) whose position relative to the irradiation target region in the CT images is the most stable for all motion phases. These are thus 'fiducials' for the target motion. The operator defines or loads the motion boundaries around the clinical target region in the CT and the computer computes the corresponding position margins for the fiducials in the ultrasound image. The same process is repeated for all the cardiac and respiratory phases used for the treatment planning.

A second, online, computer program runs during the ablation treatment and based on the input from the first computer program, searches via automatic image segmentation and registration for the position of the fiducials on the live ultrasound images. Based on this information and possibly also on the information from cardiac and respiratory motion sensors, the computer determines which cardiac and respiratory cycle phase is relevant and sends the information to the control system 2, which, if it is not already loaded, loads the corresponding irradiation plan. The computer then co-registers/fuses the position of the fiducials to those in the irradiation plan, where the target region and the safe motion boundaries are given. If the position compared to the target region is inside the safety margin, the system sends a command to the control system 2 to enable the irradiation. On the other hand, if the position compared to the target region is larger than the safety margin, the computer program sends a 'stop irradiation' to the control system 2.

While the embodiments have been described in conjunction with a number of embodiments, it is evident that many alternatives, modifications and variations would be or are apparent to those of ordinary skill in the applicable arts. Accordingly, this disclosure is intended to embrace all such alternatives, modifications, equivalents and variations that are within the scope of this disclosure. This for example particularly the case regarding the different apparatuses, which can be used.

The invention claimed is:

1. Heart arrhythmia treatment device comprising:
   a charged particle emitting system for generating a charged particle beam with required properties for ablation of a targeted tissue of a heart of a patient, the charged particle emitting system being configured to deliver a Bragg peak of the charged particle beam to the targeted tissue;
   an ultrasound cardiac imaging system configured to image a relevant region of the heart that is relevant to assess motion of the targeted tissue and corresponding cardiac and respiratory cycle phases of the patient; and
   a control system that instructs the charged particle emitting system to generate the required properties of the charged particle beam in accordance with a relevant irradiation plan and when to generate the charged particle beam based on information of the cardiac and respiratory cycle phases provided by the ultrasound cardiac imaging system, the information being acquired during a treatment stage of the patient.

2. Heart arrhythmia treatment device according to claim 1, comprising a patient positioning system which comprises a robotic treatment table and immobilization systems to position the patient.

3. Heart arrhythmia treatment device according to claim 1, comprising a verification system that includes a position imaging system for acquiring images based on double X-rays or Cone-beam Computer Tomography to verify the patient positioning.

4. Heart arrhythmia treatment device according to claim 3, wherein the control unit is configured to process ultrasound images acquired with the ultrasound cardiac imaging system:
   at a planning stage, to define fiducials of a target volume as imaged by one of a Computer Tomography system and a magnetic resonance imaging system, and,
   at the treatment stage, to determine the relevant irradiation plan for the corresponding cardiac and respiratory cycle phase, in order to quantify a difference in positions of the fiducials between the acquired ultrasound images at the treatment stage and the target volume at the planning stage.

5. Heart arrhythmia treatment device according to claim 4, wherein the control system is configured to:
determine a change in position of the target tissue based on the difference in the positions of the fiducials; and
if the change in position of the target tissue is determined to be within established safety margins according to the relevant irradiation plan, the control system enables irradiation of the target tissue.

6. Heart arrhythmia treatment device according to claim 1, wherein the charged particle beam comprises charged particles chosen from the group consisting of protons, carbon, oxygen and helium ions.

7. Heart arrhythmia treatment device according to claim 6, wherein the charged particles are protons.

8. Heart arrhythmia treatment device according to claim 1, wherein the ultrasound cardiac imaging system comprises at least one ultrasound transducer having an optical or magnetic marker coupled thereto, the optical or magnetic marker being combined with one or both of a cardiac motion sensor and a respiratory motion sensor.

9. Heart arrhythmia treatment device according to claim 1, comprising a cardiac cycle monitor and a respiratory cycle monitor working in combination with the ultrasound cardiac imaging system.

10. Heart arrhythmia treatment device according to claim 1, wherein the required properties of the charged particle beam include a specified intensity, position, angle, and energy.

11. Heart arrhythmia treatment device comprising:
a charged particle emitting system for generating a charged particle beam with required properties for ablation of a targeted tissue of a heart of a patient, the charged particle emitting system being configured to deliver a Bragg peak of the charged particle beam to the targeted tissue;
an ultrasound cardiac imaging system configured to image a relevant region of the heart that is relevant to assess motion of the targeted tissue and corresponding cardiac and respiratory cycle phases of the patient; and
a control system that instructs the charged particle emitting system when to generate the charged particle beam based on information of the cardiac and respiratory cycle phases provided by the ultrasound cardiac imaging system,
wherein, at a treatment stage, the control unit is configured to process ultrasound images acquired with the ultrasound cardiac imaging system.

12. Heart arrhythmia treatment device according to claim 11, wherein the control unit is configured, at the treatment stage, to determine the relevant irradiation plan for the corresponding cardiac and respiratory cycle phase.

13. Heart arrhythmia treatment device according to claim 11, wherein, at a planning stage, the control unit is configured to determine a position of a target volume as imaged by one of a Computer Tomography system and a magnetic resonance imaging system.

14. Heart arrhythmia treatment device according to claim 13, wherein the control unit is configured to identify positional differences between the acquired ultrasound images at the treatment stage and the images of the target volume at the planning stage.

15. Heart arrhythmia treatment device according to claim 14, wherein if the positional differences are determined to be within established safety margins according to the relevant irradiation plan, the control system enables irradiation of the target tissue.

16. Heart arrhythmia treatment device according to claim 14, wherein, at the planning stage, the control unit is configured to define fiducials of the target volume.

17. Heart arrhythmia treatment device according to claim 16, wherein the control system is configured to determine a change in position of the target tissue based on the difference in the positions of the fiducials.

18. Heart arrhythmia treatment device according to claim 11, wherein the control system instructs the charged particle emitting system to generate the required properties of the charged particle beam in accordance with a relevant irradiation plan.

19. Heart arrhythmia treatment device according to claim 11, wherein the ultrasound cardiac imaging system comprises at least one ultrasound transducer having an optical or magnetic marker coupled thereto, the optical or magnetic marker being combined with one or both of a cardiac motion sensor and a respiratory motion sensor.

20. Heart arrhythmia treatment device according to claim 11, comprising a cardiac cycle monitor and a respiratory cycle monitor working in combination with the ultrasound cardiac imaging system.

* * * * *